(12) United States Patent
Patel et al.

(10) Patent No.: US 9,458,187 B2
(45) Date of Patent: Oct. 4, 2016

(54) METHODS FOR TREATMENT OF INFLAMMATORY CONDITIONS USING S-[4-(3-FLEURO-3-METHYLBUTYRYLOXY)-BUT-2-YNYL]6α, 9α-DIFLUORO-17α-(FURAN-2-YL) CARBONYLOXY-11β-HYDROXY-16α-METHYL-3-OXOANDROSTA-1,4-DIENE-17β-CARBOTHIOATE

(71) Applicant: Sun Pharma Advanced Research Company Limited, Andheri (e) Mumbai (IN)

(72) Inventors: Jiten Ranchhodbhai Patel, Baroda (IN); Gopalkumar Chimanlal Patel, Baroda (IN); Gaurav Sanjivkumar Sheth, Baroda (IN); Sanjay Nandlal Mandhane, Baroda (IN); Chitturi Trinadha Rao, Baroda (IN); Rajamannar Thennati, Baroda (IN)

(73) Assignee: Sun Pharma Advanced Research Company Limited, Andheri (E), Mumbai (IN)

( * ) Notice: Subject to any disclaimer, the term of this patent is extended or adjusted under 35 U.S.C. 154(b) by 0 days.

(21) Appl. No.: 14/893,655

(22) PCT Filed: May 28, 2014

(86) PCT No.: PCT/IN2014/000359
§ 371 (c)(1),
(2) Date: Nov. 24, 2015

(87) PCT Pub. No.: WO2014/192027
PCT Pub. Date: Dec. 4, 2014

(65) Prior Publication Data
US 2016/0102117 A1    Apr. 14, 2016

(30) Foreign Application Priority Data
May 28, 2013   (IN) .......................... 1881/MUM/2013

(51) Int. Cl.
C07J 3/00       (2006.01)
A61K 31/56   (2006.01)
C07J 31/00     (2006.01)

(52) U.S. Cl.
CPC ................ *C07J 3/005* (2013.01); *A61K 31/56* (2013.01); *C07J 31/006* (2013.01)

(58) Field of Classification Search
CPC ................... C07J 3/00; C07J 3/005
See application file for complete search history.

(56) References Cited

U.S. PATENT DOCUMENTS 4,335,121 A      6/1982  Phillipps et al.
2009/0054388 A1* 2/2009  Patel ...................... C07J 31/006
                                                                514/179

FOREIGN PATENT DOCUMENTS

| WO | WO-2004/001369 A2 | 12/2003 |
| WO | WO-2004/039827 A2 | 5/2004 |
| WO | WO-2007/099548 A2 | 9/2007 |
| WO | WO-2014/192027    | 12/2014 |

OTHER PUBLICATIONS

"International Application No. PCT/IN2014/000359, International Search Report mailed Sep. 5, 2014", 3 pgs.

* cited by examiner

*Primary Examiner* — Paul A Zucker
(74) *Attorney, Agent, or Firm* — Schwegman Lundberg & Woessner, P.A.

(57) ABSTRACT

The present invention relates to methods of treatment of inflammatory conditions using S-[4-(3-fluoro-3-methylbutyryloxy)-but-2-ynyl]6α,9α-difluoro-17α-(furan-2-yl)carbonyloxy-11β-hydroxy-16α-methyl-3-oxoandrosta-1,4-diene-17β-carbothioate (compound of formula I), a novel anti-inflammatory compound of the androstane series and its processes of preparation.

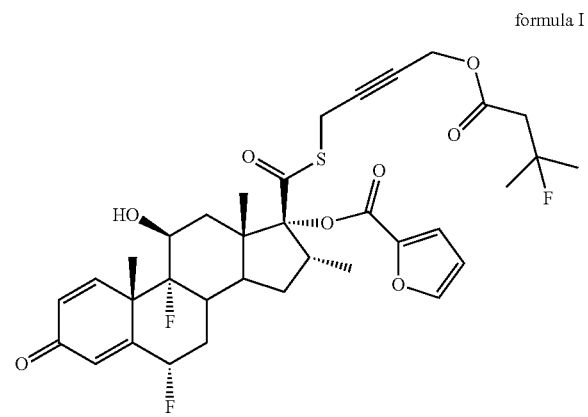

formula I

5 Claims, 7 Drawing Sheets

Figure-1: Effect of compound of formula I nasal formulation on ovalbumin-induced vascular permeability in ovalbumin sensitized and challenged guinea pigs Each bar represents the mean ± S.D. of 6 animals. $^{\psi}$Significant compared to non-sensitized control. *Significant compared to sensitized control, $p<0.05$, ANOVA followed by Dunett's test.

Figure-2: Ovalbumin-induced changes in intranasal pressure in guinea pigs

Figure-3: Effect on ovalbumin-induced conjunctival vascular permeability in guinea pigs Figure-4: Effect of Ophthalmic Steroids on IOP in Rabbits Figure-5: Scheme-I- Preparation of compound of formula I Figure-6: Scheme-II- Preparation of compound of formula I Figure 7: Scheme-III- Preparation of compound of formula I

METHODS FOR TREATMENT OF INFLAMMATORY CONDITIONS USING S-[4-(3-FLEURO-3-METHYLBUTYRYLOXY)-BUT-2-YNYL]6α, 9α-DIFLUORO-17α-(FURAN-2-YL) CARBONYLOXY-11β-HYDROXY-16α-METHYL-3-OXOANDROSTA-1,4-DIENE-17β-CARBOTHIOATE

RELATED APPLICATIONS

This application is a U.S. national stage application filed under 35 U.S.C. §371 from International Application Serial No. PCT/IN2014/000359, which was filed May 28, 2014, and published as WO2014/192027 on Dec. 4, 2014, and which claims the benefit of Indian Patent Application No. 1881/MUM/2013 filed on May 28, 2013, which applications and publication are incorporated by reference as if reproduced herein and made a part hereof in their entirety, and the benefit of priority of each of which is claimed herein.

FIELD OF INVENTION

The present invention relates to S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate, a novel anti-inflammatory compound of the androstane series and methods of treating inflammatory conditions.

BACKGROUND OF THE INVENTION

Corticosteroids (or glucocorticoids) having anti-inflammatory properties are widely used for the treatment of inflammatory conditions or disorders of skin, airways, eye, GI tract, joints, CNS etc, and several autoimmune disorders. Some of the inflammatory skin disorders where treatment with glucocorticoids is prescribed are eczema, psoriasis, allergic dermatitis, pruritis, hypersensitivity reactions etc. Inflammatory or allergic conditions of the airways for which glucocorticoids are used include disorders of nose, throat or lungs such as rhinitis (including hay fever), nasal polyps, asthma (including allergen-induced asthmatic reaction), chronic obstructive pulmonary disease, interstitial lung disease, fibrosis, etc. Glucocorticoid administration is also used for inflammatory bowel disorders such as ulcerative colitis and Crohn's diseases; and inflammatory joint disorders such as rheumatoid arthritis which are autoimmune diseases. However, administration of corticosteroids in general may cause, in addition to the desired pharmacological effect, several undesirable or adverse side effects at sites distant from the target tissue, the so-called systemic effects. The long term use of such corticosteroids is limited by the occurrence of serious undesired systemic effects including hypothalamic-pituitary-adrenal (HPA) axis suppression, widespread immunosuppression, delayed wound healing, increased bone turnover, impaired growth, muscle weakness or atrophy, peptic ulceration, skin thinning, diabetes, obesity, hypertension, water retention, progesterone and estrogen related disorders. It is therefore desirable to have glucocorticoids which possess potent anti-inflammatory activity at the target tissue, with minimal or preferably no systemic activity at therapeutic doses when used for chronic treatment.

SUMMARY OF THE INVENTION

The present invention relates to a novel glucocorticoid compound S-[4-(3-fluoro-3-methylbutyryloxy)but-2-ynyl] 6α,9α-difluoro-17α-(furan-2-yl)carbonyloxy-11β-hydroxy-16α-methyl-3-oxoandrosta-1,4-diene-17β-carbothioate of formula I formula I The compound of formula I exhibits in in vivo models for inflammation, a superior safety index as compared to compounds disclosed in prior art.

DEFINITIONS

"Safety index" refers to a measure indicative of its efficacy versus its safety. As referred to herein it is indicative of any measure indicative of its effectiveness in relation to its safety. For example, it may be measured in terms of the ratio of the dose that results in an undesired effect to that which results in a desired effect. It is commonly measured by determining the $ED_{50}$ value for a desired effect and the undesired effect and calculating the ratio of $ED_{50}$, undesired effect to $ED_{50}$, desired effect. For example, in Sephadex® lung edema model the safety index may be measured as the ratio $ED_{50}$ Thymus involution/$ED_{50}$ Lung edema. The safety index may also be expressed as the ratio of the percent desired effect to percent undesired effect at a specific dose, for example in a cotton pellet granuloma test exemplified herein, the ratio of percent inhibition of granuloma to the percent decrease in weight of thymus at a specific dose is used.

"Treating" a condition refers to taking steps to obtain beneficial or desired results, including clinical results. For purposes of this invention, beneficial or desired clinical results include, but are not limited to, alleviation or amelioration of one or more symptoms, delay or slowing of disease progression, stabilization of the disease state, and other beneficial results described below.

The term "administration" refers to systemic and/or local administration.

The term "systemic administration" refers to non-localized administration such that an administered substance may affect several organs or tissues throughout the body or such that an administered substance may traverse several organs or tissues throughout the body in reaching a target site.

The term "oral administration" used herein refers to the administration of compound via the mouth through ingestion, or via some other part of the gastrointestinal system including the esophagus. Suitable pharmaceutical, compositions for oral administration may, for example, comprise tablets (including compressed, coated or uncoated), pellets, pills, lozenges, hard or soft capsules, aqueous or oily suspensions, emulsions, dispersible powders or granules, syrups or elixirs and the like.

The term "parenteral administration" refers to and includes any route through which a compound is administered to a mammal other than through the digestive tract, non-limiting examples of such routes include: intravenous injection, intra-arterial injection, intramuscular injection, and injection through an intravenous line, cannula, catheter, and the like. Suitable pharmaceutical compositions for parenteral administration may, for example, comprise a sterile solution, suspension or emulsion for intravenous, subcutaneous, intramuscular, intra-articular, intravascular or infusion dosing and the like.

The terms "topical application" and "topically applied" are used interchangeably herein to refer to the application onto the outer layer of mammalian skin, which include application by rubbing onto the skin, brushing, painting, wiping and stroking. Suitable pharmaceutical compositions for topical administration may, for example, comprise ointments, creams, aqueous or oily solutions or suspensions transdermal patches, films, gels, lotions and the like.

The term "local administration" used herein refers to administration at or near a specific site. Suitable pharmaceutical compositions for local administration may, for example, comprise eye/ear/nose drops, creams/ointments for dermal/ophthalmic application, sprays, aerosols, powders for insufflation, inhalation, solutions/suspensions for nebulisation and the like.

The most suitable manner of administration depends in each individual case on the nature and severity of the condition to be treated and on the nature of the compound of the present invention used in each case.

DETAILED DESCRIPTION OF THE INVENTION

The present invention provides the compound of formula I. The present invention also provides methods of treating or alleviating inflammatory conditions in a patient responsive to treatment with anti-inflammatory agents comprising administering to the said patient, an effective amount of compound of the present invention. Compound of formula I may be administered in dose ranges from 0.01 mg to 10 mg. The term "dose," refers to physically discrete units that contain a predetermined quantity or amount of active ingredient administered as a single administration.

The dose of compound of the present invention used to attain the desired biological effect depends on a number of factors, for example the intended use, duration of treatment desired, the type or route of administration, frequency of dosing and the clinical state of the patient. The frequency of dosing or frequency of administration of the dose of the compound is generally once to three times daily.

In one embodiment of the present invention, the method comprises treating or alleviating inflammatory conditions or symptoms associated therewith in a human comprising administering to the said human in need thereof, an effective amount of compound of formula I.

In another embodiment of the present invention, method comprises treating or alleviating inflammatory conditions or symptoms associated with a disease selected from a group consisting of seasonal allergic rhinitis, perennial allergic rhinitis, perennial non-allergic rhinitis, chronic sinusitis, recurrent sinusitis, nasal polyps in a human comprising intra-nasally administering to the said human in need thereof, an effective amount of compound of formula I. The method relates to administration of compound of Formula I at a daily intra-nasal dose in the range from 0.01 to 2.5 mg. More preferable, method relates to administration of compound of Formula I at a daily intra-nasal dose in the range from 0.05 mg to 1.0 mg. In a preferred embodiment for treating a patient suffering from seasonal allergic rhinitis, a dose of 0.1 to 0.4 mg may be administered intranasally in a twice in a day (BID) regimen, amounting to a daily intra-nasal dose of 0.2 to 0.8 mg.

In another embodiment, method comprises treating or alleviating inflammatory conditions or symptoms associated with respiratory disorders selected from the group consisting of allergic, non-allergic and/or inflammatory diseases of the upper or lower airway passages or of the lungs like asthma, chronic obstructive pulmonary disease, bronchiolitis, croup, bronchopulmonary dysplasia, Interstitial lung disease in a human comprising administering via inhalation route to the said human in need thereof, an effective amount of compound of formula I. The dose for administration of compound of the present invention via inhalation route ranges from 0.05 mg to 10 mg.

In another embodiment, the method comprises treating or alleviating inflammatory conditions or symptoms associated with dermal disorders selected from the group consisting of eczema, psoriasis, allergic dermatitis, contact dermatitis, pruritis and hypersensitivity reactions in a human comprising administering via topical route to the said human in need thereof, an effective amount of compound of formula I.

In another embodiment, the method comprises treating or alleviating inflammatory conditions or symptoms associated with systemic inflammatory disorders selected from the group consisting of Irritable Bowel Syndrome, inflammatory bowel conditions like ulcerative colitis, Crohn's colitis, osteoarthritis or auto-immune diseases such as but not limited to rheumatoid arthritis in a human comprising administering via oral or parenteral route to the said human in need thereof, an effective amount of compound of formula I.

In yet another embodiment, the method comprises treating or alleviating inflammatory conditions or symptoms associated with ophthalmic or otolaryngological inflammatory disorders selected from the group consisting of inflammation of the eye due to allergies (such as, but not limited to, seasonal/perennial allergic conjunctivitis), chronic conditions such as keratitis, vernal kerato conjunctivitis, atopic keratoconjunctivitis, giant papillary conjunctivitis, dermatoconjunctivitis, (contact allergy), pingueculitis, and episcleritis in a human comprising administering via topical route to the said human in need thereof, an effective amount of compound of formula I.

Besides human use, the compound of the present invention may find use as an anti-inflammatory and anti-allergic agent in veterinary medicine. The compound of the present invention undergoes further clinical evaluation.

According to a further aspect of the invention there is provided a pharmaceutical composition for use in treatment of inflammatory conditions which comprises a compound of the present invention together with one or more pharmaceutically acceptable excipients or carriers.

In one embodiment, the compound of the present invention elicits potent anti-inflammatory or anti-allergic effects, particularly upon topical administration, by binding to the glucocorticoid receptor and subsequent response via that receptor.

In the in vitro receptor binding studies compound of the present invention has shown good potency and selectivity towards human glucocorticoid receptor.

In animal models of inflammation and allergy, the compound of the present invention generally displayed very good efficacy, duration of effect and surprisingly low systemic side effects. The compound of the present invention possessed the desired attributes for topical steroid such as low oral bioavailability and short systemic plasma half-life, thereby translating to low liability to systemic side effects unlike that are seen in other glucocorticoids.

The compound of present invention, when tested in in vivo models for inflammation as further described and illustrated by the way of working examples herein, exhibited significant anti-inflammatory activity with minimal side effects.

The compound of the present invention, demonstrated very high safety margin (safety index) which is several folds improved over compounds disclosed in prior art.

Process of Preparation

Another aspect of the invention is the process for the preparation of compound of formula I of the present invention.

Figure 5:
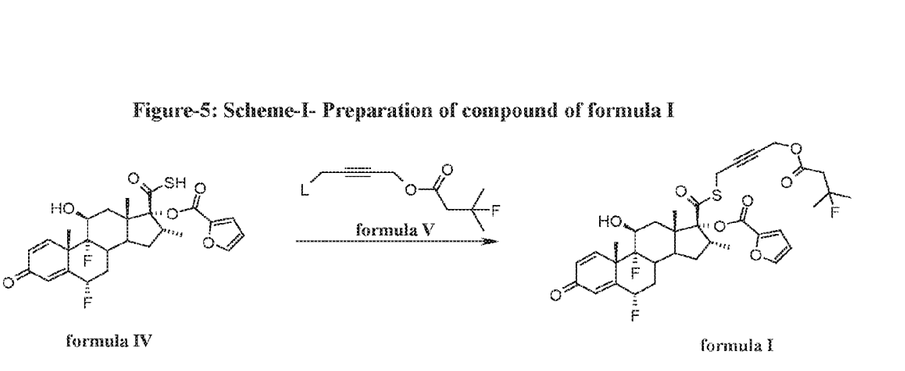
FIG. 5: Scheme I—Preparation of compound of formula I.

In one embodiment, the compound of the present invention is prepared in a single step from the thioic acid of formula IV, by alkylation with the alkyne moiety of formula V, as shown Scheme I (FIG. 5).

In the compound of formula V, L represents a leaving group (for e.g. a halogen atom, a mesyl or tosyl group, or the like), preferably L is chloro.

The alkylation reaction can be advantageously carried out in an inert organic polar solvent, for example, acetone, acetonitrile, N,N-dimethylformamide, N,N-dimethylacetamide, dimethyl sulfoxide, and the like, or mixtures thereof, preferably in acetone in presence of a suitable base. Examples of suitable bases are alkali or alkaline earth metal carbonates like potassium carbonate, sodium carbonate, sodium bicarbonate and the like, preferably potassium carbonate.

The compound of formula IV can be prepared by following known methods, for example, Gordon J. Phillips et al., J. Med. Chem., 37, 3717-3729 (1994); U.S. Pat. No. 4,335,121; PCT publication No. WO 04/001369 or WO 04/039827.

The compound of formula V may be prepared by methods known to those skilled in the art.

Figure 6:
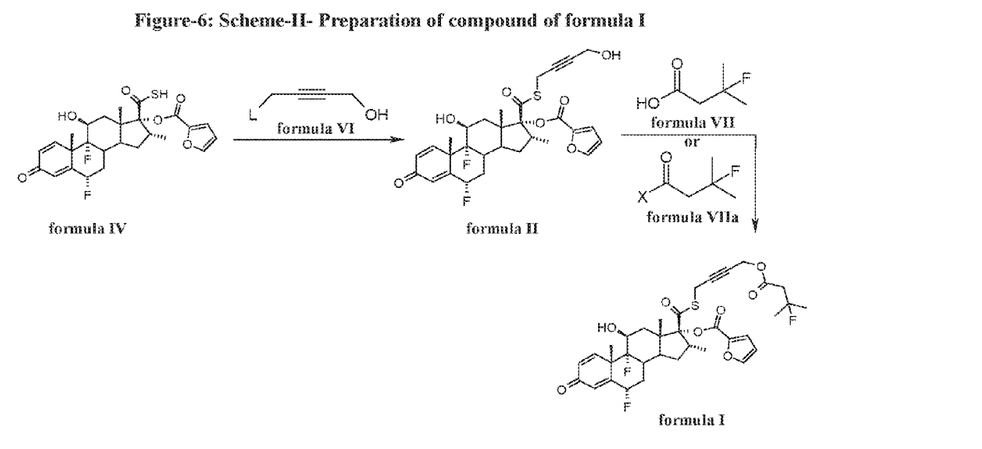
FIG. 6: Scheme II—Preparation of compound of formula I.

In another embodiment, the compound of the present invention is prepared in a two-step process as shown in Scheme II (FIG. 6).

Preparation of the compound of formula I comprise condensation of a compound of formula II with compound of formula VII in the presence of a condensating agent in an inert solvent, by methods known to those skilled in the art.

Alternatively the compound of formula VIIa, wherein X represents a halide, preferably chloro, can be used to acylate the formula II, in the presence of a suitable base, to obtain the compound of formula I.

Compound of formula II may be prepared by alkylation of compound of formula IV, with compound of formula VI, wherein L represents a leaving group (for e.g. a halogen atom, a mesyl or tosyl group, or the like), preferably L is tosyl.

The alkylation reaction can be advantageously carried out in an inert organic polar solvent, for example, acetone, acetonitrile, N,N-dimethylformamide, N,N-dimethylacetamide, dimethyl sulfoxide, and the like preferably in acetone in presence of a suitable base. Examples of suitable bases are alkali or alkaline earth metal carbonates like potassium carbonate, sodium carbonate, sodium bicarbonate and the like, preferably potassium carbonate.

Figure 7:
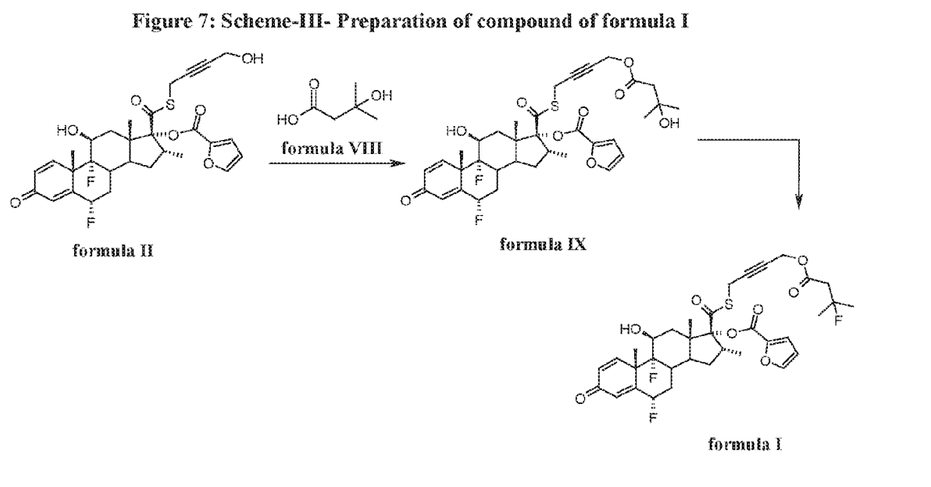
FIG. 7: Scheme III—Preparation of compound of formula I.

In yet another embodiment, the compound of the present invention is prepared in two steps from the compound of formula II shown in Scheme III (FIG. 7).

The process for preparing a compound of formula I comprise reacting a compound of formula IX with a fluorinating reagent in a suitable solvent.

Examples of fluorinating reagents include hydrofluoric acid (e.g. aqueous HF, HF-pyridine), sulfur tetrafluoride ($SF_4$), dimethylaminosulfur trifluoride, diethylaminosulfur trifluoride (DAST), morpholinosulfur trifluoride, Selectfluor® and like. Preferably the fluorination is carried out using DAST in dichloromethane solvent.

The compound of formula IX may be conveniently prepared by condensation of a compound of formula II with compound of formula VIII in the presence of an inert base and/or a suitable catalyst in an inert solvent, by methods known to those skilled in the art.

Compound of the present invention undergoes highly efficient hydrolysis to metabolite of formula II, which has similar potency in in vitro glucocorticoid receptor binding assays. However, surprisingly the compound of formula II was significantly less potent than the compound of the present invention in the topical in vivo models for anti-inflammatory efficacy such as croton oil ear edema. Both the compound of the present invention and the compound of formula II, undergo hepatic metabolism to yield the inactive metabolite, a compound of formula III. This metabolite of formula III is several fold less potent than the compound of the present invention and the compound of formula II in in vitro glucocorticoid receptor binding assays ($IC_{50}$ for formula I 2.3 nM vs 2% inhibition at 0.1 μM for formula III).

formula II

-continued formula III

The following non-limiting Examples illustrate the invention:

EXAMPLES

Example-1

S-[4-(3-Fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate A mixture of 6α,9α-difluoro-17α-(furan-2-yl)carbonyloxy-11β-hydroxy-16α-methyl-3-oxoandrosta-1,4-diene-17β-carbothioic acid (5.0 g, 9.87 mmol), 4-chloro-1-(3-fluoro-3-methylbutyryloxy)-but-2-yne (2.24 g, 10.85 mmol) and anhydrous potassium carbonate (1.5 g, 10.85 mmol) in acetone (25 ml) was stirred under a blanket of nitrogen at 25 to 30° C. for 3 hrs. DM water (100 ml) was added and stirred for 1 hr at 25-30° C. The solid obtained was filtered, washed with water and dried at 60-65° C. Resulting dry product was purification by column chromatography on silica gel (1% methanol in dichloromethane) yielded the title compound as a white solid.

$^1$H NMR (400 MHz in CDCl$_3$), δ: 1.05 (d, J=6.99 Hz, 3H), 1.20 (s, 3H), 1.36-1.40 (m, 1H), 1.46 (s, 3H), 1.51 (s, 3H), 1.55 (s, 3H), 1.74-1.98 (m, 3H), 2.28-2.53 (m, 4H), 2.68 (d, J=17.80 Hz, 2H), 2.74 (s, 1H), 3.45 (m, 1H), 3.66 (d, J=16.71 Hz, 1H), 3.76 (d, J=16.61 Hz, 1H), 4.43 (d, J=7.16 Hz, 1H), 4.54 (d, J=15.35 Hz, 1H), 4.79 (d, J=15.32 Hz, 1H), 5.33-5.49 (m, 1H), 6.40 (d, J=10.16 Hz, 1H), 6.45 (s, 1H), 6.50 (br-s, 1H), 7.12 (d, J=3.11 Hz, 1H), 7.17 (d, J=10.09 Hz, 1H), 7.59 (s, 1H).

$^{13}$C NMR (50.33 MHz in CDCl$_3$), δ: 16.94 (q), 17.76 (q), 18.45 (t), 23.63 (q, d, J=5.36), 27.32 (q, d, J=24.02), 27.53 (q, d, J=23.93), 33.27 (d, dd, J$_1$=19.35, J$_2$=11.08), 34.34 (t, d, J=21.56), 34.56 (t), 36.33 (t), 37.18 (d), 43.47 (d), 46.26 (t, d, J=25.29), 48.77 (s, dd, J$_1$=22.37, J$_2$=3.62), 49.98 (s), 53.05 (t), 72.09 (d, d, J=37.06), 76.95 (s), 82.57 (s), 87.11 (d, d, J=183.92), 93.79 (s, d, J=170.16), 97.49 (s), 99.79 (s, d, J=177.49), 112.66 (d), 119.46 (d), 147.77 (d), 121.45 (d, d, J=12.80), 130.50 (d), 144.19 (s), 152.00 (d), 157.55 (s), 162.67 (s, d, J=13.59), 170.06 (s, d, J=8.15), 195.00 (s), 186.38 (s).

IR (KBr), ν cm$^{-1}$: 3357 (br, m), 2980 (m), 2945 (m), 1727 (s), 1707 (s), 1667 (s), 1622 (m), 1606 (m), 1301 (m), 1176 (m), 992 (m), 771 (m).

Mass: 677.47 m/z [M+H]$^+$.

Example-2

S-(4-Hydroxy-but-2-ynyl)6α,9α-difluoro-17α-(furan-2-yl)carbonyloxy-11β-hydroxy-16α-methyl-3-oxoandrosta-1,4-diene-17β-carbothioate A mixture of 6α,9α-difluoro-17α-(furan-2-yl)carbonyloxy-11β-hydroxy-16α-methyl-3-oxo-androsta-1,4-diene-17β-carbothioic acid (34.0 g, 67 mmol), 4-hydroxy-1-tosyloxy-but-2-yne (17.8 g, 74 mmol) and anhydrous potassium carbonate (11.11 g, 80 mmol) in acetone (170 ml) was stirred under a blanket of nitrogen at 25-30° C. for 1 hr. The reaction mixture was quenched with DM water (500 ml) and stirred for 1 hr at 25-30° C. The solid obtained was filtered, washed with water and dried at 70-75° C. to yield the title compound as an off white solid.

¹H NMR (400 MHz in CDCl₃+DMSO-D₆) δ: 1.02 (d, J=7.08 Hz, 3H), 1.13 (s, 3H), 1.32-1.37 (m, 1H), 1.55 (s, 3H), 1.66-2.02 (m, 4H), 2.07-2.32 (m, 4H), 3.38-3.41 (m, 1H), 3.70 (d, J=16.32, 1H), 3.78 (d, J=16.35 Hz, 1H), 4.12-4.15 (m, 2H), 4.33 (d, J=6.37, 1H), 4.88 (t, J=5.92, 1H), 5.14 (m, 1H), 5.36-5.53 (m, 1H), 6.29-6.32 (m, 2H), 6.54 (dd, J₁=3.47 Hz, J₂=1.72 Hz 1H), 7.11 (d, J=3.46, 1H), 7.25 (d, J=10.45 Hz, 1H), 7.66 (m, 1H).

¹³C NMR (50.33 MHz in CDCl₃), δ: 15.79 (q), 16.70 (q), 17.70 (t), 22.66 (q, d, J=5.34 Hz), 32.10 (d, dd J₁=18.93 Hz, J₂=11.02 Hz), 33.36 (t, d, J=19.73 Hz), 33.36 (t), 34.98 (t), 36.02 (d), 42.77 (d), 47.69 (s, dd J₁=21.39 Hz, J₂=2.66 Hz), 48.85 (s), 49.18 (t), 70.31 (d, d, J=36.22 Hz), 78.09 (s), 82.39 (s), 86.15 (d, d, J=182.76 Hz), 96.64 (s), 99.12 (s, d, J=177.5 Hz), 111.78 (d), 118.39 (d), 120.01 (d, d, J=12.79 Hz), 129.14 (d), 143.15 (s), 146.94 (d), 151.07 (d), 156.31 (s), 161.73 (s, d J=12.73 Hz), 184.70 (s), 194.35 (s).

IR (KBr), ν cm⁻¹: 3546 (m), 3341 (m), 2982 (m), 2959 (m), 2936 (m), 2878 (m), 1701 (s), 1682 (s), 1657 (s), 1614 (s), 1577 (m), 1471 (s), 1393 (m), 1171 (s), 1119 (s), 1073 (s), 1019 (m), 991 (m), 891 (s).

Mass: 575.5 m/z [M+H]⁺.

Example-3

S-[4-(3-Hydroxy-3-methylbutyryloxy)-but-2-ynyl] 6α,9α-difluoro-17α-(furan-2-yl)carbonyl-oxy-11β-hydroxy-16α-methyl-3-oxoandrosta-1,4-diene-17β-carbothioate

To a stirred mixture of S-(4-hydroxy-but-2-ynyl) 6α,9α-difluoro-17α-(furan-2-yl)carbonyloxy-11β-hydroxy-16α-methyl-3-oxoandrosta-1,4-diene-17β-carbothioate (4.0 g, 6.96 mmol), 3-hydroxy-3-methylbutyric acid (1.23 g, 10.4 mmol) and triethylamine (2.9 ml, 20.8 mmol) in dry dichloromethane (50 ml) was added (benztriazol-1-yloxy)-tris-(dimethyamino)phosphonium hexafluorophosphate (BOP) (4.6 g, 10.4 mmol) and the solution was stirred at room temperature for 1 hr. The reaction mixture was poured into DM water (100 ml), the organic layer was separated and washed successively with DM water and saturated sodium chloride solution and concentrated under reduced pressure. The residue was purified by column chromatography on silica gel to yield the title compound as an off white solid.

¹H NMR (400 MHz in CDCl₃) δ: 1.05 (d, J=7.09 Hz, 3H), 1.17 (s, 3H), 1.30 (s, 3H), 1.32 (s, 3H), 1.35-1.40 (m, 1H), 1.55 (s, 3H), 1.65-1.95 (m, 3H), 2.28-2.51 (m, 4H), 2.53 (s, 2H), 3.32 (s, 1H), 3.38 (s, 1H), 3.41-3.45 (m, 1H), 3.68 (d, J=16.75 Hz, 1H), 3.76 (d, J=16.75 Hz, 1H), 4.43 (d, J=8.18 Hz, 1H), 4.69 (s, 1H), 5.32-5.49 (m, 1H), 6.39 (dd, J/=10.79 Hz, J₂=1.23 Hz, 1H), 6.45 (s, 1H), 6.50 (dd, J₁=3.15 Hz, J₂=1.40 Hz, 1H), 7.12 (d, J=3.36 Hz, 1H), 7.16 (d, J=10.12 Hz, 1H), 7.59 (s, 1H).

Mass: 674.93 m/z [M+H]⁺.

Example-4

S-[4-(3-Fluoro-3-methylbutyryloxy)-but-2-ynyl]6α, 9α-difluoro-17α-(furan-2-yl)-carbonyl-oxy-1β-hydroxy-16α-methyl-3-oxoandrosta-1,4-diene-17β-carbothioate To a stirred solution of S-[4-(3-hydroxy-3-methylbutyryloxy)-but-2-ynyl]6α,9α-difluoro-17α-(furan-2-yl)-carbonyloxy-11β-hydroxy-16α-methyl-3-oxoandrosta-1,4-diene-17β-carbothioate (3.2 g, 4.74 mmol) in dry dichloromethane (25 ml) was added N,N-diethylaminosulfur trifluoride (DAST)(0.992 g, 6.15 mmol) and the mixture was stirred 25 to 30° C. for 1.5 hrs. Quenched with DM water (100 ml), separated the organic layer and washed successively with DM water and saturated sodium chloride. Concentration under vacuum, and purification by column chromatography on silica gel (1% methanol in dichloromethane) yielded the title compound as a white solid.

Example-5

S-[4-(3-Fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate To a stirred mixture of S-(4-hydroxy-but-2-ynyl) 6α,9α-difluoro-17α-(furan-2-yl)carbonyloxy-11β-hydroxy-16α-methyl-3-oxoandrosta-1,4-diene-17β-carbo thioate (0.59 g, 1 mmol), 3-fluoro-3-methylbutyric acid (0.25 g, 2 mmol) and 4-(dimethylamino)pyridine (0.025 g, 0.2 mmol) in dry acetonitrile (20 ml) was added 1-ethyl-3-(3-dimethyllaminopropyl)carbodiimide hydrochloride (EDC HCl) (0.79 g, 4.1 mmol) was added and the mixture stirred at room temperature for 4 hrs. The reaction mixture was quenched with DM water (100 ml), the product extracted into ethyl acetate (100 ml), washed successively with a DM water and saturated sodium chloride solution. Concentration under reduced pressure and purification of the residue by column chromatography on silica gel (1% methanol in dichloromethane) yielded the title compound as an off white solid.

Pharmacological Data

Example-6

Steroid Receptor Binding Assays

The activity of test compounds on glucocorticoid receptor was assessed using radioligand binding assays. The human HeLa cells transfected with glucocorticoid receptors were incubated with [$^3$H]dexamethasone at 25° C. for 2 hrs in RPMI-1640, 10 nM HEPES, pH 7.2 incubation medium, in the absence or presence of test compounds at 3 nM and/or 10 nM concentration. Free [$^3$H]dexamethasone was removed from the medium by centrifugation and concentration of receptor bound ligand was determined in the supernatant by liquid scintillation counting.

Dexamethasone as reference compound was tested concurrently as an integral part of each assay to ensure the validity of the results obtained. The % inhibition was evaluated using a single concentration of test compound and the corresponding radiolabeled ligand. Results are presented as the percent inhibition of specific binding. The values are average of duplicate determinations for each concentration.

For determination of binding to other related steroidal receptors by compound of the present invention cloned receptors from cells indicated in the parentheses were used: estrogen Erα/Erβ and progesterone (human recombinant insect Sf9), testosterone (human LnCAP) and aldosterone (Wistar rat kidney).

TABLE 1

Human Glucocorticoid receptor binding (in vitro) screen

| Compound | $IC_{50}$ | $K_i$ |
| --- | --- | --- |
| Formula I | 2.3 nM | 1.24 nM |
| Dexamethasone | 4.71 nM | 2.54 nM |

TABLE 2

Steroidal receptor binding (in vitro) screen

| Compound | Receptor class/Type | Species | $IC_{50}$ | $K_i$ |
| --- | --- | --- | --- | --- |
| Formula I | Aldosterone | Rat | 328 nM | 256 nM |
| | Progesterone | Human | 8.52 nM | 3.29 nM |
| | Progesterone | Bovine | 39.4 nM | 5.14 nM |
| | Estrogen Erα | Human | No significant binding at 100 nM | — |
| | Estrogen Erβ | Human | No significant brinding at 100 nM | — |
| | Testosterone | Rat | No significant binding at 100 nM | — |

In above indicated in vitro receptor binding study, the compound of the present invention has shown good potency and selectivity towards human glucocorticoid receptor when compared with other steroidal receptors such as aldosterone, estrogen, progesterone and testosterone receptors (refer Tables-1 & 2).

Example-7

Croton Oil Ear Edema

Mice (male, CD-1) were made into different groups. A method similar to one reported in the literature was used. Test compounds were dissolved in pyridine-water-acetone (4:2:14) solution 10 μl of this solution of compound or vehicle solution was applied to the left ear of the mice. The right ear of each mouse was applied simultaneously with 10 μl of pyridine: water: acetone (4:2:14) solution. After 2 hrs of compound or vehicle application, 10 μl of croton oil solution was applied to the left ear of all animals. After 6 hr of croton oil treatment the animals were sacrificed; ears were excised and weighed separately.

TABLE 3

| Croton oil ear edema screen | |
|---|---|
| Compound | Inhibition of ear edema (%) |
| Formula I | 75.5 (1 µg) |
| Fluticasone propionate | 81.09 (1.6 µg) |
| Dexamethasone | 50.05 (1.6 µg) |

Compound of the present invention exhibited significant inhibition of ear edema at a lower dose.

Example-8

Cotton Pellet Granuloma

SD rats were used for assessing anti-inflammatory activity of test compound using cotton pellet granuloma method. Sterilized cotton pellets weighing 20 mg were prepared. Test compounds were dissolved in acetone so as to get the required quantity for each cotton pellet in 500 µl. Different pellets were impregnated with 500 µl of acetone to contain required quantity of test compounds and allowed to dry. Vehicle control pellets were impregnated with 500 µl acetone.

Rats were made into different groups. Two cotton pellets were surgically implanted into the scapular region of each rat. On sixth day of such implantation, pellets along with granuloma were taken out. Thymus gland was also separated from each animal and weighed. The pellets with granuloma were dried for 20 hrs at 60° C. and weighed. Mean weights of dry granuloma and thymus, body weight gain/100 g body weights were calculated.

TABLE 4

| Cotton pellet granuloma test | | | |
|---|---|---|---|
| Compound | Dose (mcg/pellet) | Mean % Inhibition of Granuloma A | Thymus wt. (% Decrease) B | Ratio A/B* |
| Formula I | 100 | 58.13 | 4.67 | 12.44 |
| Ciclesonide | 100 | 63.38 | 15.16 | 4.18 |
| Fluticasone propionate | 100 | 66.04 | 73.56 | 0.89 |

*The ratio A/B gives an indication of the measure of safety index

In above indicated cotton pellet granuloma model, the systemic side effect markers such as the thymus involution and the body weight gain were insignificant even at dose levels of 100 mcg per pellet. The safety index for the compound of the present invention, measured as the ratio of inhibition of granuloma to extent of thymus involution, was much superior when compared to marketed topical corticosteroids such as ciclesonide and fluticasone propionate.

Example-9

Skin Atrophy and Systemic Side Effects in Rats on Topical Application

Male SD rats were lightly anesthetized with isoflurane. Bilaterally paired sites were marked on the back, one on each side of the flank. One of the sites was applied with an appropriate dose of compound of the present invention and fluticasone propionate dissolved in the acetone, daily for a period of 14 days. Contralateral site served as solvent treated controls and received acetone. Body weights were monitored on 0-14 days. On day 15, twenty-four hours after the last applications, blood was collected from the tail vein to determine total and differential blood cell count. The animals were euthanized and full-thickness skin from shaved area was punched to get 15 mm diameter plugs. The subcutaneous fat and muscle was removed and the punched plug was weighed. Thymus weights of each animal were also determined as a marker of systemic corticosteroid activity

TABLE 5

Effect of 2-week dermal application of compound of formula I and fluticasone propionate on skin thickness, thymus weight, body weight gain and leukocyte counts in rats

| Treatment | Dose (µg/site) | % Inhibition | | | | | % Body Weight Gain |
| | | Skin weight | Thymus | Total leukocyt | Lymphocytes | Neutrophils | |
|---|---|---|---|---|---|---|---|
| Vehicle | — | — | — | — | — | — | 72.4 |
| formula I | 6 | 0.0 | 0.0 | 0.0 | 0.0 | 0.0 | 82.4 |
| | 18 | 0.0 | 0.0 | 0.6 | 0.0 | 0.0 | 80.8 |
| | 60 | 0.0 | 0.0 | 0.0 | 0.0 | 0.0 | 75.6 |
| | 180 | 0.0 | 0.0 | 0.0 | 0.0 | 0.6 | 80.4 |
| Fluticasone propionate | 6 | 25.3 | 2.0 | 31.4 | 31.7 | 25.8 | 68.1 |
| | 18 | 20.8 | 5.4 | 17.5 | 15.9 | 24.5 | 67.4 |
| | 60 | 27.9 | 23.0 | 15.2 | 15.6 | 14.5 | 61.9 |
| | 180 | 30.0 | 55.0 | 32.7 | 34.1 | 24.6 | 42.5 |

Values of inhibition as compared to organ weights or cell counts in the vehicle treatment group. All values in compound of formula I treatment group were statistically non-significant compared to vehicle control groups When evaluated in above indicated animal models for local and systemic side effects upon dermal application, the compound of the present invention did not cause either skin atrophy or systemic immunosuppressive effect at doses upto 180 mcg, unlike fluticasone propionate used as a reference corticosteroid. The change in weight in the thymi is a measure of systemic activity and thereby of toxicity. Lower the weight of the thymi, the greater the systemic toxicity. From the data provided in Table 5, upon 2-week of dermal application of compound of the present invention did not cause any inhibition of the thymus weight even at high doses, thereby indicating that the compounds of the present invention have much less systemic activity.

Example-10

Sephadex®-Induced Lung Edema in SD Rats

Sephadex® G-200 was prepared in sterile saline (10 mg/ml) and allowed to swell for at least 3 days at room temperature. Test compounds were were administered intratracheally at 24 hrs and 2 hrs prior to intratracheal administration of Sephadex® (5 mg/kg) under light ether anesthesia. Vehicle control animals were administered vehicle instead of Sephadex®. At 24 hr after Sephadex® instillation, lung and thymus were excised from individual animals and weighed. Wet weights of lungs and thymus were corrected for 100 g of initial body weight. The percentage increase in lung weight caused by Sephadex® and its inhibitions by the compounds, were calculated. The percentage inhibitions of thymus compared to vehicle control group were also calculated

TABLE 6

Safety index for compounds in Sephadex ® lung edema model in SD rats

| Compound | $ED_{50}$ Lung edema inhibition (mg/kg, i.t.) | $ED_{50}$ Thymus involution (mg/kg, i.t.) | Safety index $ED_{50}$ Thymus involution/$ED_{50}$ Lung edema |
|---|---|---|---|
| Formula I | 0.094 | 8.70 | 92.55 |
| Ciclesonide | 0.388 | 3.13 | 8.07 |
| Budesonide | 0.101 | 0.68 | 6.73 |
| Fluticasone propionate | 0.086 | 0.36 | 4.19 |

In above indicated animal model for lung inflammation, viz. Sephadex® induced lung inflammation model, the compound of the present invention was found to be either superior or comparable in efficacy when compared to reference corticosteroids such as budesonide, ciclesonide and fluticasone propionate. Also, in terms of systemic safety profile (thymus involution used as a marker), the compound of the present invention was surprisingly much superior to these reference drugs, thereby exhibiting a relatively high safety index (ratio of efficacy to side effect i.e. the separation of local anti-inflammatory activity from the systemic activity). The safety index of compound of the present invention was found to be several folds higher than that of fluticasone propionate.

Example-11

Liver Glycogen Deposition in Rats

Male Sprague Dawley rats, weighing 190-220 g were bilaterally adrenalectomized and maintained on 0.9% saline solution throughout the experiment. On day 5th and 6th of adrenalectomy, animals were made into different groups, test compounds prepared in cold saline (sonicated for 30 min) were instilled intratracheally 2 doses @3 mg/kg, 24 hrs apart. At 15 hrs after the last treatment, animals were sacrificed and livers were excised and weighed. The glycogen content of the livers was determined by anthrone method. Briefly, a weighed quantity of liver tissue was homogenized with 5% trichloroacetic acid, supernatant mixed with ethanol and kept overnight for precipitation. The glycogen thus extracted was estimated as glucose generated after acid hydrolysis by addition of anthrone reagent at 620 nm. Glycogen content was expressed as mg/100 g liver.

TABLE 7

Liver Glycogen deposition in rats

| Compound | Dose (mg/kg) | Glycogen content (mg/100 g liver) | % Inhibition of thymus |
|---|---|---|---|
| Formula I | 3 | 10.68 | 26.15 |
| Fluticasone propionate | 3 | 1514.65 | 70.17 |
| Mometasone furoate | 3 | 1117.32 | 43.51 |
| Budesonide | 3 | 552.77 | 65.02 |
| Ciclesonide | 3 | 263.96 | 61.34 |

In above indicated study, the lack of undesired systemic side effects for the compound of the present invention was further demonstrated by measuring hepatic glycogen deposition in rats following intratracheal administration. The hepatic glycogen deposition, which is a measure of the metabolic systemic side effect of glucocorticoids, was extremely insignificant for the compound of the present invention when compared with that for reference corticosteroids such as budesonide, ciclesonide and fluticasone propionate. This clearly demonstrates the minimal systemic toxicity and the potent anti-inflammatory activity of the compound of the present invention.

Example-12

Inhibition of Ovalbumin-Induced Nasal Vascular Permeability in Guinea Pigs

Figure 1:
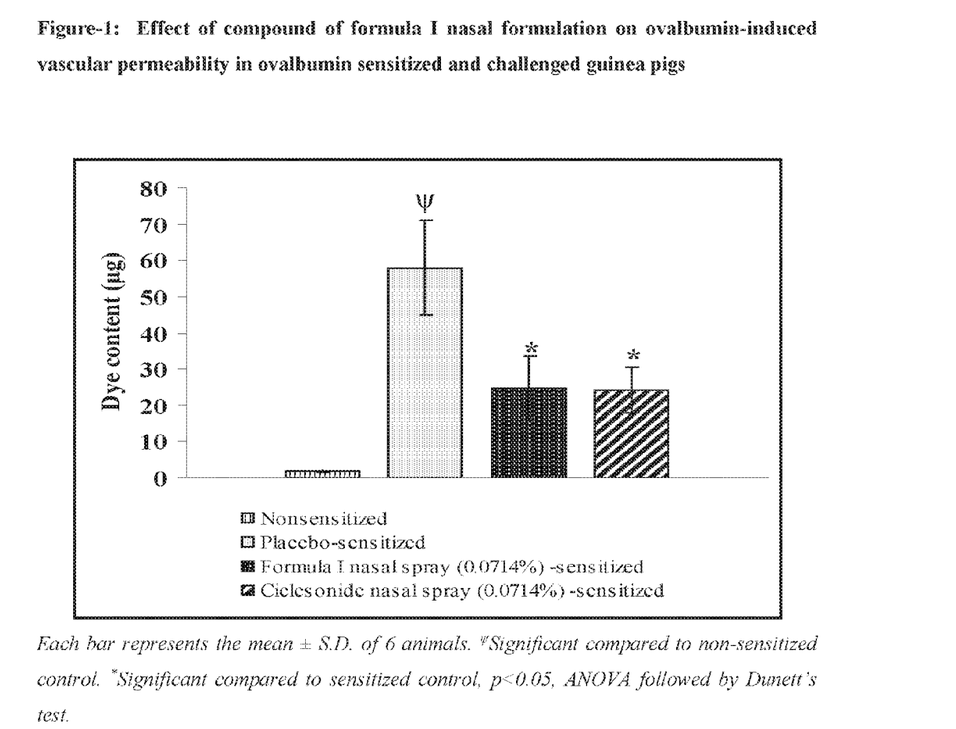
FIG. 1: Effect of compound of formula I nasal formulation on ovalbumin-induced vascular permeability in ovalbumin sensitized and challenged guinea pigs

Allergic rhinitis was induced by sensitization with intraperitoneal injection of ovalbumin (100 µg/0.5 ml/animal) suspended in aluminum hydroxide gel every week for 4 weeks, followed by topical instillation of 60 mg/ml, 20 µl/nostril ovalbumin solution. In successfully sensitized animals, 40 µl of compound of formula I (0.0714%), ciclesonide (0.0714%), and placebo were instilled into both nostrils of respective group and eight hr after animals were anesthetized with pentobarbital sodium (50 mg/kg, i.p.). The esophagus was ligated and the oral cavity was sealed with a bioadhesive. Tracheotomy was performed for spontaneous breathing and the nasopharynx was catheterized connected to the perfusion pump set to deliver a rate of 0.25 ml/min. Evans blue dye (3% w/v, 1 ml/kg) was administered intravenously. The nasal cavity was perfused with ovalbumin (1%) for a period of 10 min, and saline for a period of 50 min. The perfusate was collected for 60 min. Supernatant of the perfusate was estimated for dye content spectrophotometrically at 620 nm. Extravasation of intravenously administered Evans blue dye was monitored as a marker of vascular permeability. The total amount of dye leakage into the nasal cavity over the 60 min time duration was calculated. Intranasal administration of compound of formula I nasal formulation at 28.56 µg/nostril dose, 8 hr prior to ovalbumin-challenge reduced the ovalbumin-induced dye leakage. The reference formulation ciclesonide also caused inhibition of dye leakage similar to compound of formula I nasal formulation. These results are presented in FIG. 1.

Example-13

Inhibition of Ovalbumin-Induced Increase in Intranasal Pressure in Guinea Pigs

Figure 2:
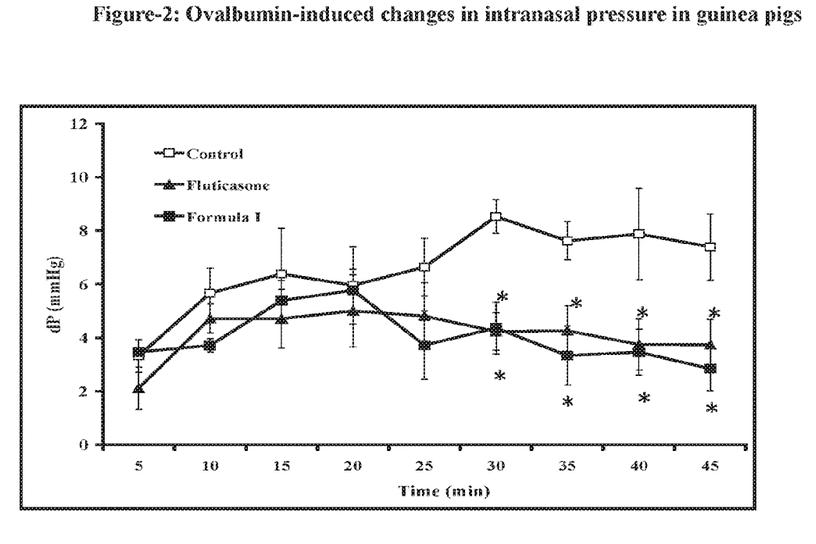
FIG. 2: Ovalbumin-induced changes in intranasal pressure in guinea pig

Animals sensitized with ovalbumin as described above were used for experiments determining intranasal pressure. Intranasal instillation of compound of formula I, fluticasone propionate or placebo was done 24 hr and 2 hr prior to challenge with ovalbumin. The nasopharynx was catheterized with a PE cannula, one end of which was attached to pressure transducer and other to the nebulizer. Ovalbumin (5%) was nebulized into the nasal cavity for 10 min. The changes in intranasal pressure were recorded for following 45 min and differential pressure (dP) was calculated. Compound of formula I and fluticasone propionate caused equivalent inhibition of intranasal pressure as shown in FIG. 2.

Therefore, in above indicated in vivo models for allergic inflammation of upper respiratory tract, such as ovalbumin-induced vascular permeability and ovalbumin-induced increase in intranasal pressure in sensitized guinea pigs, the compound of the present invention was found to have efficacy comparable to that of marketed topical corticosteroids such as ciclesonide and fluticasone propionate.

Example-14

Efficacy in Allergen-Induced Conjunctivitis in Guinea Pigs

Figure 3:
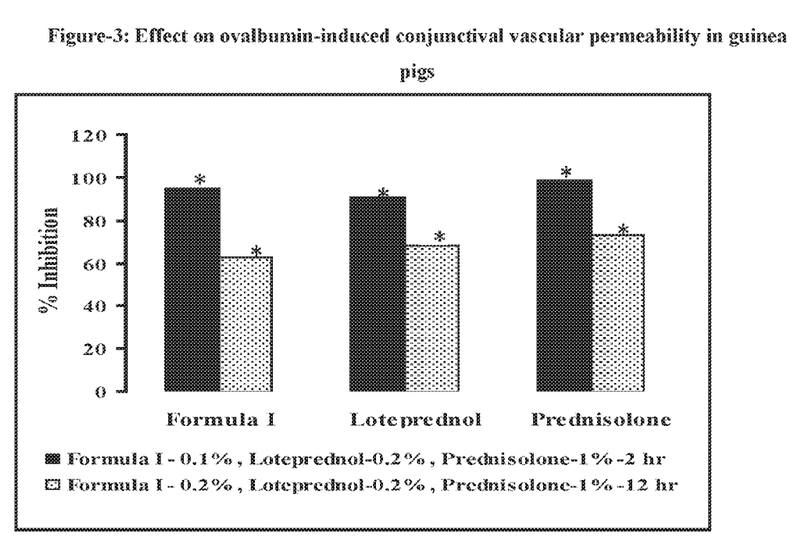
FIG. 3: Effect on ovalbumin-induced conjunctival vascular permeability in guinea pigs

Guinea pigs were sensitized by intraperitoneal ovalbumin (100 µg/animal, aluminum hydroxide as an adjuvant) were used in these experiments. Two doses of compound of formula I, loteprednol etabonate, prednisolone acetate or placebo were instilled into the right eye of different guinea pigs at 3 hr intervals. Two hrs after the second instillation of steroid formulations; Evans blue dye (0.5%, 4 ml/kg, i.v.) was administered through jugular vein and immediately thereafter the eye was challenged with ovalbumin and eyelids were removed, dye was extracted using a 5 ml solution of acetone and sodium sulfate and was quantified spectrophotometrically at 620 nm (results are represented in FIG. 3—Effect on ovalbumin-induced conjunctival vascular permeability in guinea pigs).

In above indicated animal model for ocular allergic inflammation viz. allergen-induced conjunctivitis in guinea pigs, the compound of the present invention showed efficacy comparable to the reference ophthalmic corticosteroids viz. lotepredol etabonate and prednisolone.

Example-15

Effect on Intraocular Pressure (IOP) in Rabbits

Figure 4:
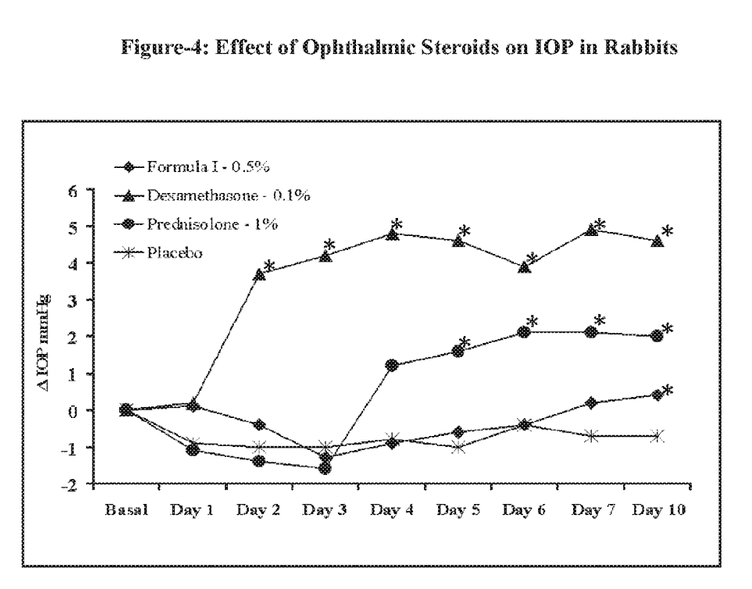
FIG. 4: Effect of ophthalmic steroids on IOP in rabbits

Ophthalmic instillation of 40 µl of compound of formula I, loteprednol etabonate, dexamethasone sodium phosphate, and placebo were undertaken in different group of animals, 10 instillations daily at an interval of 1 hour for 10 days. IOP measurement was performed 1 hr after instillation of the last dose (results are represented in FIG. 4—Effect of ophthalmic steroids on-IOP in rabbits).

In the case of the compound of the present invention as per above study, the intraocular pressure (IOP), a side effect for potent ophthalmic corticosteroids, was insignificant (comparable to placebo) when compared with reference corticosteroids dexamethasone and prednisolone. Further, when administered by intranasal route in allergen sensitized animals, the allergen-induced increase in intranasal pressure, an indicator of intranasal resistance, is inhibited by compound of the present invention.

Example-16

Efficacy and Safety by Intranasal Administration

The present study was conducted to determine the efficacy and safety of the compound of the present invention via intranasal route in Seasonal Allergic Rhinitis model. This was a single-centered, randomized, double-blind, placebo-controlled parallel group study.

OBJECTIVE: The objective of the study was to assess the efficacy and safety of the compound of the present invention via intranasal route compared to placebo in alleviating the signs and symptoms of Seasonal Allergic Rhinitis in Environmental Exposure Chamber Model (EEC) after 2 weeks of treatment.

METHODS: In this study, male and female patients aged 18-65 years with history of seasonal allergic rhinitis and positive skin prick test to *Dactylis* glomerate within 12 months prior to screening and with TNSS score of >6 at least once during the 2 hour-screening EEC were included. Total 159 patients were included in the study and total 154 patients were considered for efficacy analysis. 39 patients received 200 µg (100 µg BID), 37 patients received 400 µg (200 µg BID), 39 patients received 800 µg (400 µg BID) of the compound of the present invention via nasal route and 39 patients received vehicle as placebo.

Primary efficacy endpoint was change in TNSS (Total Nasal Symptom Score) in a 4-hour environmental challenge with *Dactylis* glomerate pollen in an EEC from baseline to Day 15/16. The TNSS was calculated as summation of 4 point severity scale (0=None, 1=Mild, 2=Moderate and 3=Severe) for each symptom (Nasal congestion, Rhinorrhea, Nasal itching and Sneezing).

Secondary efficacy endpoint was change in TNSS subscales and change in the amount of nasal secretion in a 4-hour environmental challenge in an EEC from baseline to Day 15/16. Safety endpoint was incidence of treatment-emergent adverse events.

The results showed that there was no significant difference in the safety profile of the compound of the present invention and the Placebo. All the doses of the compound of the present invention were statistically superior to the placebo for all primary and secondary efficacy endpoints and that the compound of the present invention was safe and effective for the treatment of seasonal allergic rhinitis.

The invention claimed is:

1. A compound of the formula I formula I

2. A process for preparing a compound of formula I comprising alkylation of a compound of formula IV with alkyne moiety of formula V, wherein, in the compound of formula V, L is a leaving group.

3. A process for preparing a compound of formula I,

Comprising:
a. alkylation of a compound of formula IV with a compound of formula VI, wherein L is a leaving group, to obtain a compound of formula II and,
b. treating the compound of formula II with a compound of formula VII or a compound of formula VIIa wherein X in compound of formula VIIa is halide.

4. A process for preparing a compound of formula I, formula I comprising:
a. acylating a compound of formula II formula II with a compound of formula VIII formula VIII to obtain a compound of formula IX formula IX and
b. Fluorinating the compound of formula IX.

5. A method of treating or alleviating inflammatory conditions or symptoms associated therewith in a human comprising administering to the said human in need thereof, an effective amount of compound of formula I formula I

* * * * *

UNITED STATES PATENT AND TRADEMARK OFFICE
CERTIFICATE OF CORRECTION

PATENT NO. : 9,458,187 B2
APPLICATION NO. : 14/893655
DATED : October 4, 2016
INVENTOR(S) : Patel et al.

It is certified that error appears in the above-identified patent and that said Letters Patent is hereby corrected as shown below:

On the Title Page

Item (54), and in the Specification, in Column 1, Line 3, in "Title", delete "S-[4-(3-FLEURO" and insert --S-[4-(3-FLUORO--, therefor Item (71), in "Applicant", in Column 1, Line 3, after "Mumbai", insert --, Maharashtra--, therefor In the Claims In Column 20, Line 1, in Claim 3, delete "Comprising:" and insert --comprising:--, therefor Signed and Sealed this
Nineteenth Day of June, 2018

Andrei Iancu
*Director of the United States Patent and Trademark Office*